United States Patent [19]

James

[11] 4,116,195

[45] Sep. 26, 1978

[54] DEVICE FOR DISPENSING MEDICAMENTS

[75] Inventor: Michael James, Welwyn Garden City, England

[73] Assignee: Allen & Hanburys Limited, London, England

[21] Appl. No.: 767,518

[22] Filed: Feb. 10, 1977

[30] Foreign Application Priority Data

Feb. 10, 1976 [GB] United Kingdom ............... 5098/76

[51] Int. Cl.² ........................................... A61M 15/00
[52] U.S. Cl. .................................. 128/266; 128/208; 222/193; 222/83.5
[58] Field of Search ................... 128/208, 206, 266; 222/83.5, 87, 88, 193

[56] References Cited

U.S. PATENT DOCUMENTS 3,906,950  9/1975  Cocozza ............................. 128/206
3,949,751  4/1976  Birch et al. ......................... 128/208

Primary Examiner—Henry J. Recla
Attorney, Agent, or Firm—William R. Liberman

[57] ABSTRACT

An inhalation device for self-administration to a patient powdered medicaments contained in a capsule. A chamber receives a capsule containing a powdered medicament. The chamber has a nozzle through which air from the chamber can be inhaled and the air inlet apertures leading into the chamber and so arranged that the air flow caused by inhalation through the nozzle will cause the capsule to be agitated. A magazine is slidable in the chamber to and from an operative position and is also rotatable in the chamber. The magazine has therein a capsule loading passage and at least one other passage. A capsule piercing needle and a capsule ejecting member are so arranged and positioned inside the chamber that the said passages can be registered as desired with either the needle or the ejector member on rotation of the magazine and so that movement of the magazine to the operative position will cause a capsule in a passage registered with the needle to engage the needle and be pierced by it and will cause a capsule in a passage registered with the ejector member to be engaged by the member thereby to displace the capsule from its passage into the chamber so that the powdered medicament from the pierced capsule can be aspirated through the nozzle by the inhalation of the patient.

7 Claims, 4 Drawing Figures

DEVICE FOR DISPENSING MEDICAMENTS

BACKGROUND OF THE INVENTION

It is well known to administer powdered medicaments to the lung bronchioles of a patient by means of inhalation devices having mouthpieces which enable the medicament to be inhaled through the mouth of the patient. The medicament is supplied in capsules which are inserted in the device and pierced prior to use, after which inhalation through the mouthpiece will cause the powdered medicament to be released from the capsule and passed to the patient. An object of the present invention is to provide an improved such inhalation device which is particularly, but not exclusively, suitable for use in the treatment of asthmatic patients.

The inhalation device is primarily intended for the oral administration of a medicament, in which case the nozzle is a mouthpiece which may be inserted in the mouth of a patient. However, the device can be used for the nasal administration of a medicament in which case the nozzle is constructed so that it may be inserted in a nostril of a patient.

BRIEF DESCRIPTION OF THE ACCOMPANYING DRAWINGS

DESCRIPTION OF A PREFERRED EMBODIMENT

Figure 1:
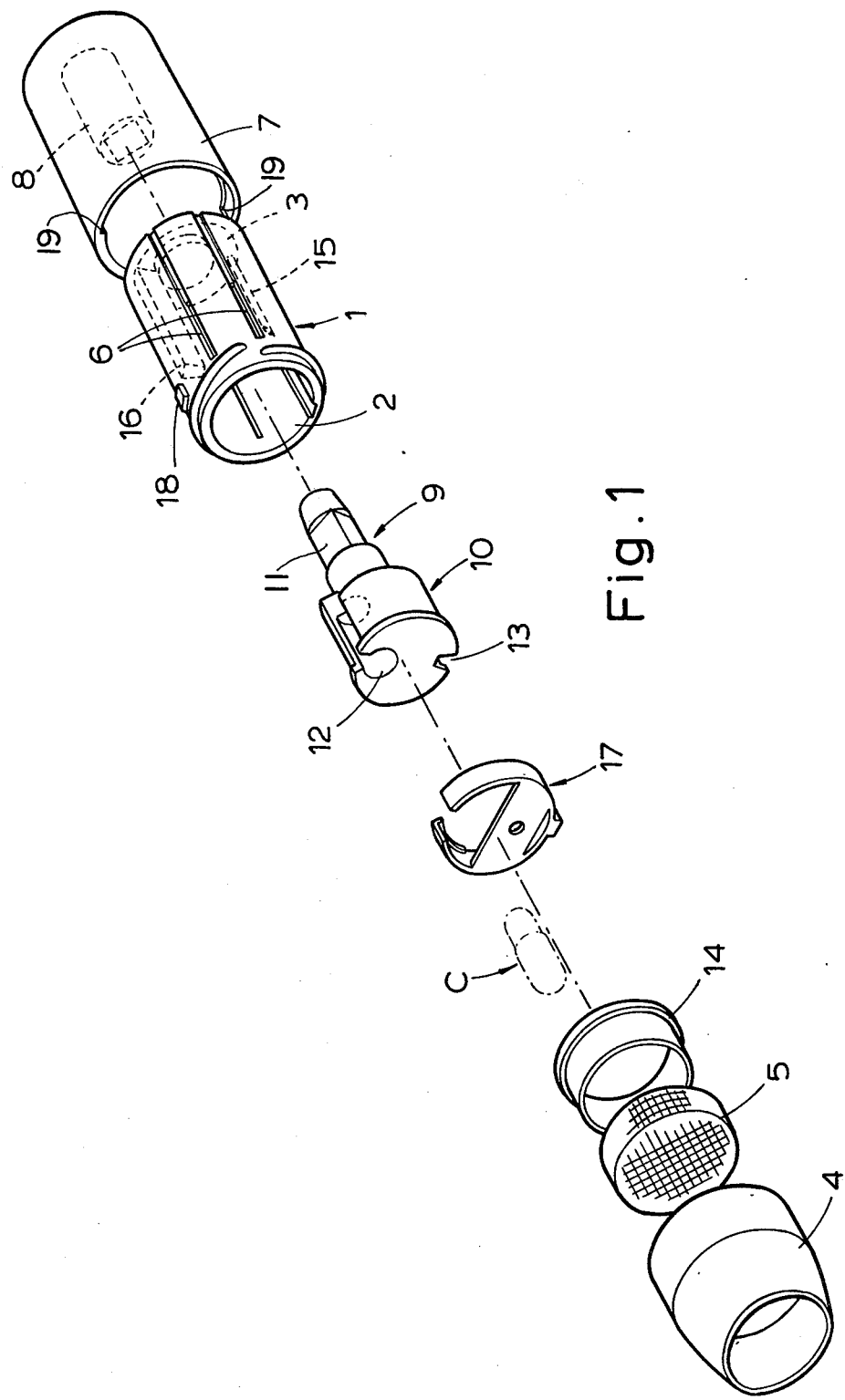
FIG. 1 is an exploded perspective view of an inhalation device.
Figure 2:
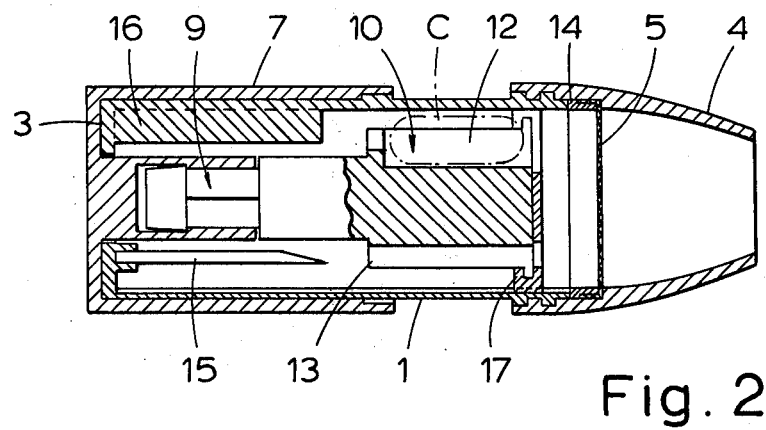
FIGS. 2 and 3 are sectional views of the same views showing parts thereof in two different positions.
Figure 3:
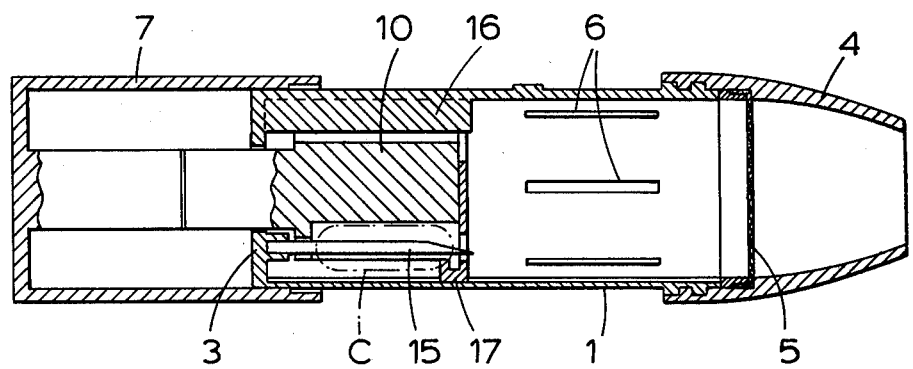

In the embodiment of the invention illustrated in FIGS. 1 to 3, an inhalation device for the oral administration of a medicament comprises a cylindrical body 1, the interior of which defines a chamber 2 arranged to receive a capsule C (FIGS. 2 and 3) containing powdered medicament. The body 1 has an annular wall 3 at one end and is open at the other end. For convenience of description the end of the body with the annular wall 3 is herein considered to be the rear end and the open end is considered to be the front end. A tubular mouthpiece 4 is removably fitted on the front end of the body. The mouthpiece 4 is provided with a grid or guard 5, which may be of gauze, which prevents a capsule C in the chamber 2 being withdrawn through the mouthpiece 4 when a patient inhales through the mouthpiece. The grid or guard is retained in the mouthpiece 4 by a retaining ring 14. The grid or guard 5 may have a rough surface in which case it also has the function that as a capsule C tends to run round it, vibrations will be produced in the capsule which will tend to vibrate and disperse the powder. The cylindrical wall of the body 1 is provided with a plurality of air inlet slots 6 leading into the chamber 2 and running lengthwise of the body 1. Conveniently, there are not less than two or more than four slots. These air inlet slots 6 are angled with respect to a diametrical cord of the chamber in such a way that, when air is inhaled through the mouthpiece 4, a spiral, turbulent air flow will be produced in the chamber 2. If a capsule C is in the chamber 2 the air flow through the chamber 2 will cause the capsule to be violently agitated. If the capsule C is pierced prior to inhalation, such agitation will cause the powder in the capsule to be released and dispersed in the turbulent airflow. The resulting powder dispersion will then pass to the patient through the mouthpiece 4.

An operating sleeve 7 is mounted on the outside of the body so as to be telescopically slidable over the rear portion of the body 1. The sleeve 7 has near its rear end a passage 8 of reduced diameter which receives a central shaft 9 of a capsule dispensing magazine or barrel 10. The barrel 10 is conveniently of cylindrical cross-section. The shaft 9 has a flat portion 11 complementary to a similar portion in the passage 8 so that when the shaft is engaged in the passage, the barrel will rotate when the sleeve 7 is rotated. The barrel has two passages 12, 13 extending lengthwise of the barrel 10 and the body 1. The axes of these passages are equidistant from the axis of the barrel. The passages are open at both ends of the barrel. One of the passages 12 is a capsule loading passage which may be loaded with a capsule by removing the mouthpiece and inserting a capsule into the capsule loading passage 12 through the open front end of the passage after which the mouthpiece is again fitted on the front end of the body.

Fixed inside the annular end wall 3 of the body and projecting forwards therefrom are a capsule piercing needle 15 and a capsule ejecting fin 16. The needle 15 and the fin 16 are so positioned that either of the passages 12, 13 in the barrel can be registered with them by appropriate rotation of the barrel.

When the sleeve 7 is in a closed or inoperative position (FIG. 2) the end wall of the sleeve abuts against the end wall 3 of the body. When the sleeve is in this position, the barrel is positioned just forward of the forward ends of the capsule piercing needle 15 and the capsule ejector fin 16. When the barrel is in that position, the capsule loading passage 12 is loaded with a capsule C and the barrel 10 is then rotated by rotation of the sleeve 7 to register the capsule in that passage 12 with the capsule piercing needle 15. The sleeve 7 is then moved to the open or operative position (FIG. 3). This draws the capsule C on to the needle 15 which will therefore penetrate the capsule and if opening movement is continued for a sufficient distance the needle will pass through both ends of the capsule. When the capsule is registered with the capsule piercing needle it is also positioned adjacent a retaining ring or plate 17 at the front end of the barrel. During a capsule piercing operation, a portion of the retaining ring or plate is registered with the capsule loading passage 12 so that the needle cannot push the capsule out of its passage. During such movement to pierce the capsule, the capsule ejector fin 16 will have entered the other passage 13 in the barrel, such passage 13 not containing any capsule. When the capsule has been pierced, the sleeve 7 and barrel 10 are then moved to the closed position and rotated to register the capsule loading passage 12 with the ejector fin 16 after which the sleeve is again moved to the open or operative position so that the fin 16 will engage the capsule and push it through the capsule outlet hole into the chamber 2 inside the body. Movement of the sleeve 7 to the open or operative position also uncovers the slot 6.

In order to limit rotation of the sleeve 7 so that it cannot be rotated beyond positions in which the capsule loading passage 12 is registered with either the fin 16 or the needle 15 the body has an external stop 18 which is engageable by an abutment 19 inside the sleeve.

When the pierced capsule has been ejected into the chamber the patient can the inhale through the mouthpiece so as to draw into himself the powdered medicament from the capsule. After completion of the inhalation operation the mouthpiece can be removed to enable the spent capsule to be removed.

DESCRIPTION OF MODIFICATIONS

Figure 4:
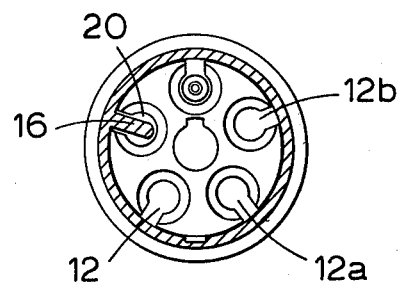
FIG. 4 is a sectional view of a modified device.

In a modification illustrated in FIG. 4, the barrel 10 has more than two passages, so that it has a plurality of capsule loading passages 12, 12a, 12b. The barrel can then be loaded with a plurality of capsules which are pierced by the needle and ejected into the chamber by the ejector fin as desired by suitable rotation of the barrel. In such an arrangement, it is necessary when the barrel is initially loaded with capsules to have one passage 20 which is not loaded with a capsule thereby to enable the ejector fin 16 to enter that passage during the first piercing operation.

If desired, the sleeve can have a ratchet fitting on the body so that it can be rotated only in one direction and also so that a positive click is felt each time the sleeve has been rotated a predetermined amount.

The sleeve 7 serves as a handle by which the dispenser can be held. If desired, the dispenser can be modified by omitting the sleeve 7 and extending the shaft 9 of the barrel 10 outwards of the rear end of the body. A handle is in the form of a knob which can be arranged on the outer portion of the shaft to enable the barrel to be rotated and moved lengthwise of the body.

What is claimed is:

1. An inhalation device for self-administration to a patient powdered medicaments contained in a capsule, the said device comprising:
    (a) a housing defining a chamber adapted to receive a capsule containing a powdered medicament, said housing having a nozzle communicating with the interior of the chamber through which air from said chamber can be inhaled and air inlet means defining apertures formed in said housing for causing air to flow through said apertures said chamber and through said nozzle and thereby, causing said capsule to be agitated;
    (b) a magazine slidably mounted in said chamber and longitudinally slidable to and from an operative position, said magazine being also rotatable about a longitudinal axis in said chamber, and having therein a longitudinal capsule loading passage and at least one other longitudinal capsule loading passage circumferentially spaced from said capsule loading passage, said passages being eccentric equidistantly to said axis means for sliding and rotating said magazine in said chamber;
    (c) means including a capsule piercing needle and a capsule ejecting member circumferentially spaced from said needle and mounted to said housing and so arranged and positioned inside said chamber that said passages can be registered simultaneously one with said needle and the other with said ejector member or vice versa, on rotation of said magazine and so that movement of said magazine to said operative position will cause a capsule in one of said passages registered with said needle to engage said needle and be pierced by it or will cause a capsule in one of said passages registered with said ejector member to be engaged by said member thereby to displace the capsule from said passage into said chamber so that the powdered medicament from the pierced capsule can be aspirated through said nozzle by the inhalation of the patient; and
    (d) means for preventing the capsule leaving said chamber when the patient inhales through said nozzle.

2. A device as claimed in claim 1 wherein said magazine has a plurality of capsule loading passages.

3. A device as claimed in claim 1 wherein said housing comprises a cylindrical body and said means for sliding and rotating includes an operating sleeve telescopically slidably mounted over an end portion of said body and rotatable thereon, said magazine being cylindrical and mounted to said sleeve and located inside the chamber so that said magazine is rotatable and slidable with said sleeve.

4. A device as claimed in claim 3 wherein said sleeve defines a handle by which the device can be held by a patient.

5. A device as claimed in claim 3, wherein said nozzle is a mouthpiece through which a patient can inhale and is arranged at a front end of said body and said sleeve is slidable over the rear end of said body, the rear end of the body having an annular end wall through which extends a shaft connecting said magazine with said sleeve.

6. A device as claimed in claim 5, wherein said needle extends forwards of said annular end wall and said ejector member is a fin extending lengthwise along the internal wall of the body defining said chamber, the circumferential spacing of the passages and between the needle and fin being equal as are their radial distance from the longitudinal axis of said magazine and chamber.

7. A device as claimed in claim 5, wherein said needle extends forwards of said annular end wall and said ejector member is a fin extending lengthwise along the internal wall of the body defining said chamber.

* * * * *